(12) United States Patent
Borlongan et al.

(10) Patent No.: US 8,618,167 B2
(45) Date of Patent: Dec. 31, 2013

(54) METHODS OF ATTENUATING COGNITIVE DEFICITS WITH SULFONYL FLUORIDES

(75) Inventors: Cesario V. Borlongan, Augusta, GA (US); Donald E. Moss, El Paso, TX (US); Isabel C. Sumaya, Bakersfield, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 1499 days.

(21) Appl. No.: 10/218,893

(22) Filed: Aug. 14, 2002

(65) Prior Publication Data
US 2003/0087959 A1 May 8, 2003

Related U.S. Application Data

(60) Provisional application No. 60/345,156, filed on Nov. 6, 2001.

(51) Int. Cl.
*A01N 37/00* (2006.01)
*A61K 31/185* (2006.01)

(52) U.S. Cl.
USPC .......................................................... 514/553

(58) Field of Classification Search
USPC ........................................ 514/649, 709, 553
See application file for complete search history.

(56) References Cited

U.S. PATENT DOCUMENTS 5,395,822 A * 3/1995 Izumi et al. ........................ 514/3
5,798,392 A * 8/1998 Moss ............................ 514/649

OTHER PUBLICATIONS

Moss et al., "Methanesulfonyl fluoride, a highly selective CNS inhibitor of acetylcholinesterase, improves passive avoidance performance after ischemia in rats," Society for Neuroscience Abstracts, 26:Abstract No. 860.14, 2000.*
Hardman, J. G., Editor-in-Chief, Goodman & Gilman's the Pharmacological Basis of Therapeutics, Ninth Edition, 1996, pp. 513 and 514.*
Giacobini, E. "Present and Future of Alzheimer therapy", Abstract of J. Neural Transm. (Suppl. 59, 231-242, 2000.*
Cornwell et al. Enhanced trauma program commitment at a level I Trauma Center. Arch Surg. 2003; 138:838-843; abstract only.*
Gittleman et al. Emergency endovascular interventions of traumatic cranial and extracranial injuries. Semin. Intervent. Radiol. 2003;20:151-168, abstract only.*
Tarrago SB. Prevention of choking, strangulation, and suffocation in childhood. WMJ. 2000; 99(9):43-6, 42; abstract only.*
Flanagan et al. Use of N-acetylcysteine in clinical toxicology. Am J Med. 1991;91(3C):131S-139S, abstract only.*
Yeoh et al. Carbon monoxide and cyanide poisoning in fire related deaths in Victoria, Australia. J Toxicol Clin Toxicol. 2004; 42(6):855-63, abstract only.*
Kraus JF. Effectiveness of measures to prevent unintentional deaths of infants and children from suffocation and strangulation. Public Health Rep. 1985; 100(20:231-240; see p. 231, col. 1, first two columns.*

(Continued)

*Primary Examiner* — Daniel Sullivan
*Assistant Examiner* — Trevor Love
(74) *Attorney, Agent, or Firm* — Fulbright & Jaworski LLP

(57) ABSTRACT

The present invention provides for methods of treating cognitive deficits resulting from interruption of blood supply and/or oxygen deficit by administering a therapeutically effective dose of a sulfonyl fluoride, such as methanesulfonyl fluoride and ethanesulfonyl fluoride. The underlying cause of the or oxygen deficit can be from stroke, trauma, carbon monoxide poisoning, and other poisonings. This method also includes co-administering with sulfonyl fluoride with a therapeutically effective dose of a second agent.

15 Claims, 6 Drawing Sheets

(56) References Cited

OTHER PUBLICATIONS

The Compact Oxford English Dictionary. AskOxford.com. p. 1.*
Scremin et al, Survival under hypoxia, Age dependence and effect of cholinergic drugs, 1980, Stroke, 11, pp. 548-552 (6 pages, including title page).*
Giacobini, E., "Cholinesterase Inhibitors Stabilize Alzheimer's Disease," *Ann. N.Y. Acad. Sci.*, 920: 321-327, 2000.
Moss et al., "Methanesulfonyl fluoride, a highly selective CNS inhibitor of acetylcholinesterase, improves passive avoidance performance after ischemia in rats," *Society for Neuroscience Abstracts*, 26: Abstract No. 860.14, 2000.
Palacious-Esquivel et al., "Methanesulfonyl fluoride (MSF) blocks scopolamine-induced amnesia in rats," *Neurology of Aging*, 14:93-96, 1993.
Aharon-Peretz et al., Behavioral differences between white matter lacunar dementia and Alzheimer's disease: a comparison on the neuropsychiatric inventory, *Dement. Geriatr. Cogn. Disord.*, 11:294-8, 2000.
Ballatore et al., "Tau-mediated neurodegeneration in Alzheimer's disease and related disorders," *Nature Neuroscience Reviews*, 8:663-72, 2007.
Bär et al., "Influence of galantamine on vasomotor reactivity in Alzheimer's disease and vascular dementia due to cerebral microangiopathy," *Stroke*, 38:3186-92, 2007.
Billeci et al., "Hormone replacement therapy and stroke," *Curr. Vasc. Pharmacol.*, 6:112-23, 2008.
Borlongan et al., "Methanesulfonyl fluoride, an acetylcholinesterase inhibitor, attenuates simple learning and memory deficits in ischemic rats," *Brain Res.*, 1038:50-8, 2005.
Conant and Schauss, "Therapeutic applications of citicoline for stroke and cognitive dysfunction in the elderly: a review of the literature, " *Altern. Med. Rev.*, 9:17-312, 2004.
Fujiki et al., "Neuroprotective effect of donepezil, a nicotinic acetylcholine-receptor activator, on cerebral infarction in rats," *Brain Res.*, 1043:236-41, 2005.
Ginestet et al., "Donepezil induces a cholinergic sprouting in basocortical degeneration," *J. Neurochem.*, 102:434-40, 2007.
Ginsberg, "The new language of cerebral ischemia," *AJNR Am. J. Neuroradiol.*, 18:1435-1445, 1997.
Haass and Selkoe, "Soluble protein oligomers in neurodegeneration: lessons from the Alzheimer's amyloid beta-peptide," *Nature Reviews Mol. Cell. Biol.*, 8:101-12, 2007.
Kranenburg et al., "Beta-amyloid (Abeta) causes detachment of N1E-115 neuroblastoma cells by acting as a scaffold for cell-associated plasminogen activation," *Mol. Cell. Neurosci.*, 28:496-508, 2005.
LaFerla et al., "Intracellular amyloid-beta in Alzheimer's disease," *Nature Neuroscience Reviews*, 8:499-509, 2007.
Lo, "A new penumbra: transitioning from injury into repair after stroke," *Nature Medicine*, 14:497-500, 2008.
Lukatela et al., "Dementia rating scale performance: a comparison of vascular and Alzheimer's dementia," *J. Clin. Exp. Neuropsychol.*, 22:445-54, 2000.
Martinez-Vila et al., "Neuroprotection in vascular dementia," *Cerebrovasc Dis.*, 21 Suppl. 2:106-17, 2006.
Mattson. "Pathways towards and away from Alzheimer's disease," *Nature*, 430:631-9, 2004.
Medina et al., "Tissue plasminogen activator mediates amyloid-induced neurotoxicity via Erk1/2 activation," *EMBO J.*, 24:1706-16, 2005.
Mungas et al., "The effects of age on rate of progression of Alzheimer disease and dementia with associated cerebrovascular disease," *Arch. Neurol.*, 58:1243-7, 2001.
Nakamura, "Aniracetam: its novel therapeutic potential in cerebral dysfunctional disorders based on recent pharmacological discoveries," *CNS Drug Rev.*, 8:70-89, 2002.
O'Neill et al., "The role of neuronal nicotinic acetylcholine receptors in acute and chronic neurodegeneration," *Curr. Drug Targets CNS Neurol. Disord.*, 1:399-411, 2002.
Peng et al., "1-3-n-Butylphthalide improves cognitive impairment induced by chronic cerebral hypoperfusion in rats," *JPET*, 321:902-10, 2007.
Ryan et al., "Hormonal treatment, mild cognitive impairment and Alzheimer's disease," *Int. Psychogeriatr.*, 20:47-56, 2008.
Sare et al., "Association between hormone replacement therapy and subsequent arterial and venous vascular events: a meta-analysis," *Eur. Heart J.*, 29:2031-41, 2008.
Saver, "Proposal for a Universal Definition of Cerebral Infarction," *Stroke*, 39:3110-31 15, 2008.
Scremin and Jenden, "Effects of middle cerebral artery occlusion on cerebral cortex choline and acetylcholine in rats," *Stroke*, 20:1524-30, 1989.
Scremin and Jenden, "Time-dependent changes in cerebral choline and acetylcholine induced by transient global ischemia in rats," *Stroke*, 22:643-7, 1991.
Tanzi, "The synaptic Abeta hypothesis of Alzheimer disease," *Nature Neuroscience*, 8:977-9, 2005.
Tohgi et al., "Cerebrospinal fluid acetylcholine and choline in vascular dementia of Binswanger and multiple small infarct types as compared with Alzheimer-type dementia," *J. Neural. Transm.*, 103:1211-20, 1996.

* cited by examiner

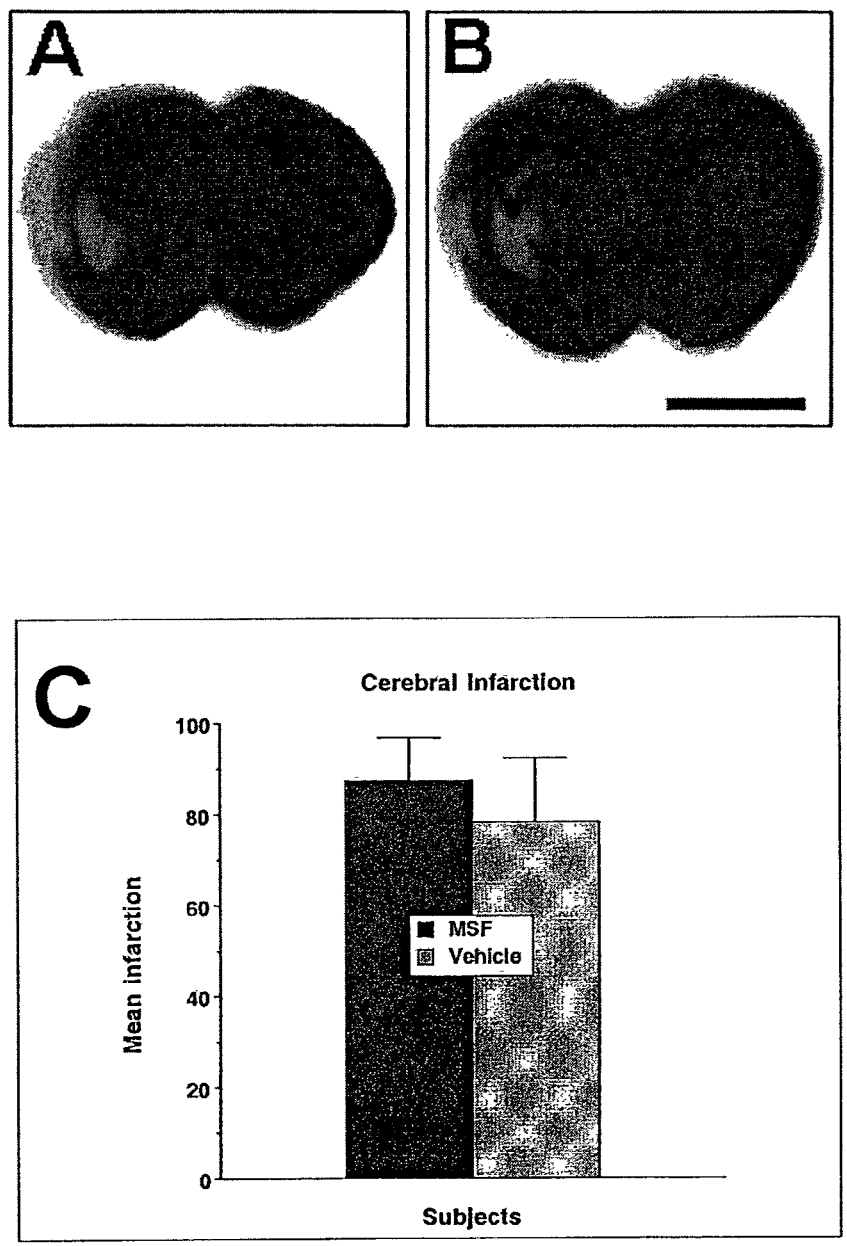
FIG. 2A-C

METHODS OF ATTENUATING COGNITIVE DEFICITS WITH SULFONYL FLUORIDES

The present application claims benefit of priority to U.S. Provisional Ser. No. 60/345,156, filed Nov. 6, 2001, the entire contents of which are hereby incorporated by reference.

BACKGROUND OF THE INVENTION

A. Field of the Invention

The present invention relates generally to the fields of neurology and the pharmacotherapy. In particular, the present invention provides methods of improving cognitive deficits which occur following stroke and other conditions which interfere with the brain receiving the necessary blood supply or oxygen.

B. Description of the Related Art

The central nervous system (CNS) is highly vulnerable to ischemic injury. Because the CNS neurons are solely dependent on the glucose and oxygen delivered by the blood (Siesjo et al., 1976), inadequate blood supply or "stroke" can easily trigger degeneration of CNS neurons. Stroke is one of the leading causes of death in Western, as well as, Asian countries. In the U.S., stroke sufferers total 700,000, and 30% of these stroke-afflicted patients die, while another 20-30% become severely and permanently disabled. Current treatments for stroke patients are drug therapies that provide for clot removal and cell survival maintenance. No drugs are currently used for the persistent dementia syndrome subsequent to stroke.

Two major types of drugs have been demonstrated to produce some beneficial effects against stroke. One type of drugs is utilized to ensure continuous blood flow to the CNS after a stroke by dissolving blood clots, and these include the anticoagulants or thrombolytics such as aspirin, heparin, and platelet inhibitors (Schellinger et al., 1997). Another group of drugs, appropriately called "cell maintenance drugs," is principally used to block neuronal degenerative processes. These drugs are NMDA receptor blockers, calcium channel blockers, caspase inhibitors, protein kinase inhibitors, free radical scavengers, and neurotrophic factors (Endres et al., 1998; Nishino et al., 1998; Wang et al., 1997). The limited efficacy of these drugs is primarily due to the narrow window of rescuing ischemic CNS neurons (Lee et al., 1999).

The unpredictable nature of the majority of stroke cases means that treatment cannot be initiated until the injury becomes apparent. Moreover, identification of the stroke as ischemic or hemorrhagic is critical to the potential benefit of thrombolytic drugs; treatment of a hemorrhagic stroke with thrombolytic drugs could lead to excessive bleeding and may be fatal to the patient. On the other hand, cell maintenance drugs can temporarily support cell integrity, but they may not correct the stroke-induced energy deficit nor block secondary neurodegenerative mechanisms. Thus, thrombolytic and cell maintenance drugs can only promote partial protection or a delay in the onset of degeneration.

Patients who survive acute stroke are left with motor, verbal, cognitive or affective dysfunctions. Unfortunately, a less concerted research effort in the treatment of stroke is provided for rehabilitation of the survivors. Recently, the need for exercise training or a similar physical therapy program for stroke survivors has been shown to aid in recovery of lost motor skills (Dobkin, 1998; Macko et al., 1997), but restoration of cognitive functions in stroke survivors has been less examined.

The problem, however, has been to develop an effective, relatively nontoxic inhibitor for acetylcholinesterase (acetylcholinesterase, EC 3.1.1.7), the enzyme widely accepted as involved in memory functions (Deutsch, 1971; Drachman and Glosser, 1981). Cholinesterase inhibitors, in general, are a relatively toxic compounds because significant inhibition of these enzymes in peripheral tissues are associated with nausea, vomiting, diarrhea, excessive salivation, and other signs of excessive cholinergic activity. In addition there is some evidence that inhibition of butyrylcholinesterase (BchE, E.C. 3.1.1.8), concurrently with acetylcholinesterase (AchE, E.C. 3.1.1.7), potentiates the toxicity of cholinesterase inhibitors in peripheral smooth muscle (Reutter et al., 1987). The ideal cholinesterase inhibitor to be used for the treatment of a chronic disease such as cognitive impairment would, therefore, be selective for the CNS (compared to peripheral tissues), be long acting, and have a high degree of selectivity for acetylcholinesterase (compared to butyrylcholinesterase).

Methanesulfonyl fluoride (MSF) is a long-acting irreversible inhibitor of acetylcholinesterase that shows excellent selectivity for the CNS (Moss et al., 1988; Moss et al., 1985). This selectivity seems to be due, in part, to the irreversible mechanism of action. Recovery from irreversible inhibition is a simple function of the rate of new synthesis of acetylcholinesterase in each tissue. Fortunately, acetylcholinesterase in the brain is resynthesized at a rate much slower than peripheral tissues (Moss et al., 1988; Moss et al., 1985). Therefore, methanesulfonyl fluoride can be used to accumulate up to 80-90% inhibition of rodent and monkey brain acetylcholinesterase with minimum inhibition of peripheral enzyme and without toxicity by using relatively small doses of the drug over a long period of time (Moss et al., 1988; Moss et al., 1985).

Methanesulfonyl fluoride also has high selectivity as an inhibitor of acetylcholinesterase in comparison to butyrylcholinesterase and is much better with regard to this quality than tacrine, metrifonate, and physostigmine which do not show this high degree of selectivity (Pacheco et al., 1995). This may also be one mechanism by which methanesulfonyl fluoride avoids peripheral toxicity. In summary, therefore, methanesulfonyl fluoride is a long-acting, acetylcholinesterase-selective inhibitor that can produce up to 80-90% inhibition in the brain without toxicity.

Despite the research discussed above, there are significant problems in this art in determining whether a potential therapeutic pharmaceutical will be clinically efficacious in humans. The results given below show that treatment with MSF produces functional effects in adult rats subjected to an experimental stroke model.

SUMMARY OF THE INVENTION

Thus, in accordance with the present invention, there is provided a method of treating cognitive deficits in a mammal comprising the step of administering to the mammal a therapeutically effective dose of a sulfonyl fluoride selected from the group consisting of methanesulfonyl fluoride and ethanesulfonyl fluoride. The mammal may in particular suffer from a cognition deficit after an interruption in blood supply and/or oxygen deficit in the brain. The interruption in blood supply and/or oxygen deficit may be caused by stroke, trauma, carbon monoxide poisoning, and other poisonings. The dose of sulfonyl fluoride may be about 0.01 mg/kg to about 20 mg/kg, about 0.05 mg/kg to about 5 mg/kg, or about 0.15 mg/kg to about 0.5 mg/kg. The sulfonyl fluoride may be administered in a pharmaceutically acceptable excipient.

The method may further comprising co-administering with said sulfonyl fluoride a second therapeutic agent, such as an agent selected from the group consisting of glutamate release modulators, acetylcholine synthesis enhancers, nicotinic agonists, muscarinic agonists, thrombolytic agents, a cholesterol reducing agent, an anti-excitotoxic N-methyl-D-aspartate antagonist, a calcium channel blocker, a cholinergic agonist, a caspase inhibitor, a free radical scavengers, or a protein kinase inhibitor. The thrombolytic agent may be heparin, aspirin, or a platelet inhibitor, the anti-excitotoxic N-methyl-D-aspartate antagonist may be MK-801, the cholinergic agonist may be RS86, the acetylcholine synthesis enhancer may be lecithin, and the glutamate release modulator may be 4AP.

In another embodiment, there is provided a method of increasing choline aceytltransferase activity a mammal comprising the step of administering to said mammal a dose of a sulfonyl fluoride selected from the group consisting of methanesulfonyl fluoride and ethanesulfonyl fluoride, the dose effective to increase the activity of choline aceytltransferase in the mammal. The dose of sulfonyl fluoride may be about 0.01 mg/kg to about 20 mg/kg, about 0.05 mg/kg to about 5 mg/kg, or about 0.15 mg/kg to about 0.5 mg/kg. The sulfonyl fluoride may be administered in a pharmaceutically acceptable excipient.

In yet another embodiment, there is provided a method of reducing one or more stroke-induced deficits in a mammal comprising the step of administering to the mammal a dose of a sulfonyl fluoride selected from the group consisting of methanesulfonyl fluoride and ethanesulfonyl fluoride, the dose effective to reduce one or more stroke-induced deficit.

In still yet another embodiment, there is provided a method of reducing stroke-induced loss of function in a tissue distal to the stroke site in a mammal comprising the step of administering to the mammal a dose of a sulfonyl fluoride selected from the group consisting of methanesulfonyl fluoride and ethanesulfonyl fluoride, the dose effective to protect from stroke-induced loss of function at said distal tissue.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-2C: The effect of MSF in cerebral infarction. There was no significant difference in the total volume of cerebral infarction between MSF- and vehicle-treated ischemic animals (shown in FIGS. 2A and 2B, respectively) as revealed by triphenyl-tetrazolium chloride staining. Mean volumes of infarction (FIG. 2C) are expressed in mm$^3$±S.E.M. The scale bar is 1 cm.

DETAILED DESCRIPTION

A. The Present Invention

Figure 1A:
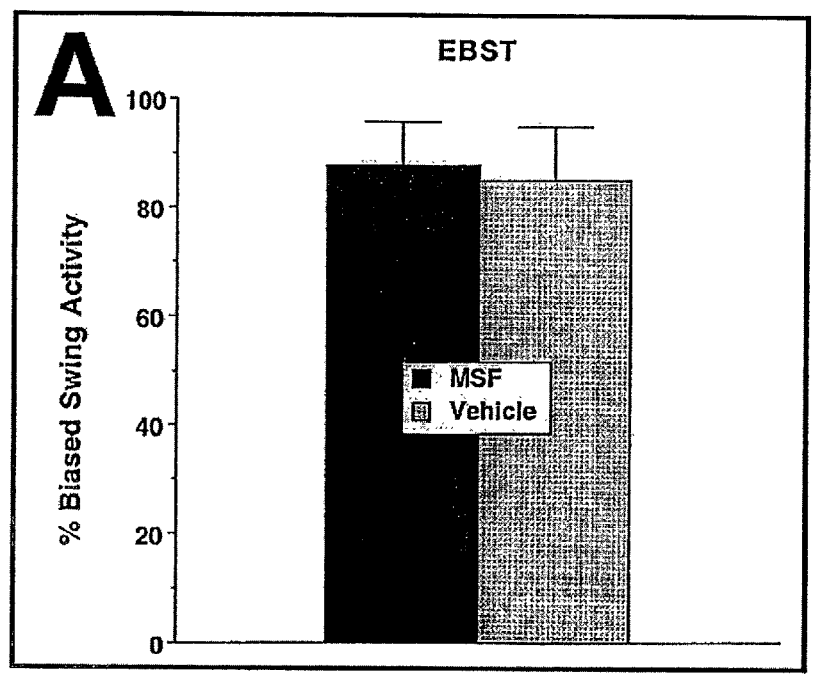
FIGS. 1A & 1B: MSF functional effects. Both groups of ischemic animals that received MSF or vehicle displayed significant motor asymmetry as revealed by elevated body swing test (EBST) (FIG. 1A). However, MSF-treated ischemic animals exhibited near normal acquisition and retention of the passive avoidance task compared to vehicle-treated ischemic animals (FIG. 1B). The first set of bars represents the mean total of time to acquire the task, while the second set of bars indicate mean step down latency. Data are expressed in means±S.E.M. Asterisk (*) indicates significance at p<0.05.

Methanesulfonyl fluoride (MSF), a highly selective CNS inhibitor of acetylcholinesterase, has been recently demonstrated to promote improvement in cognitive performance in patients with senile dementia of Alzheimer type. U.S. Pat. No. 5,798,392. However, there is no neuropathological basis for predicting that sulfonyl fluorides would be effective in treating cognitive decline subsequent to stroke. Furthermore, even though sulfonyl fluorides are thought to act primarily as cholinesterase inhibitors, recent evidence suggests that they may also increase choline acetyltransferase in the brain.

Because cognitive impairment sometimes accompanies stroke, the inventors investigated whether treatment with MSF could produce beneficial effects in adult rats subjected to an experimental stroke model. Sprague-Dawley rats received transient, 60-min, intraluminal occlusion of the right middle cerebral artery (MCAo) and were given i.p. injections of either MSF (1 mg/kg at 24 and 48 hrs post-MCAo and 0.3 mg/kg thereafter every other day) or the vehicle, peanut oil, for four weeks. The MSF treatment produced about 90% inhibition of acetylcholinesterase in the brain. Ischemic animals that received the vehicle displayed motor asymmetries and impaired cognitive performance as revealed by the elevated body swing test (EBST) and the passive avoidance test, respectively. Interestingly, while the ischemic animals that received the MSF exhibited motor asymmetries, they performed significantly better in the passive avoidance task than the vehicle-treated animals. Moreover, whereas brains from both groups of animals revealed similar extent and degree of cerebral infarction, the MSF-treated animals showed more intense septal choline acetyltransferase immunoreactivity than the vehicle-treated animals. The present results show that MSF, possibly by preserving a functional cholinergic system, attenuated stroke-induced cognitive deficits.

B. Definitions

The term "effective amount" refers to the amount of a sulfonyl fluoride in a formulation that is necessary to improve the mental status of an individual with stroke-induced cognitive deficit. The precise amount required will vary depending upon the particular compound selected, the age and weight of the subject, route of administration, and so forth, but may easily be determined by routine experimentation, as described below in the examples. In general, however, an effective amount will range from about 0.01 mg/kg to about 20 mg/kg, preferably about 0.05 mg/kg to about 5 mg/kg, and most preferably about 0.15 to about 0.5 mg/kg.

The term "pharmaceutically acceptable" refers to a compound, such as a salt or excipient, which is not unacceptably toxic to the subject to which it is administered. Pharmaceutically acceptable salts include inorganic anions such as chloride, bromide, iodide, sulfate, sulfite, nitrate, nitrite, phosphate, and the like. And organic anions such as acetate, malonate, pyruvate, propionate, cinnamate, tosylate, and the like. Pharmaceutically acceptable excipients are described at length in Remington's Pharmaceutical Sciences.

The term "cognitive deficit" includes one or more of the following: loss of or important deterioration in short-term and/or long-term memory or loss of or important deterioration in learning ability, lose of executive functions (rational decision making, judgement), decline in the ability to carry out activities of daily living, personality changes, and hallucinations or delusions. Cognitive decline in learning means significantly prolonged period of time required to acquire new skills or information, and a decline in memory means significantly shortened periods for retaining such skills or information.

The term treatment means lessening one or more cognitive deficits in a subject.

C. Pharmaceutical Compositions and Routes of Administration

Pharmaceutical compositions containing a sulfonyl fluoride may contain one or more pharmaceutical carriers. The term "pharmaceutically acceptable carrier" refers to any generally acceptable excipient that is relatively inert, non-toxic and non-irritating. Because sulfonyl fluorides are minimally soluble and relatively unstable in water, the product should be dissolved in an oil miscible carrier. A sulfonyl fluoride also may be administered in an emulsion. When the carrier serves as a diluent, it may be solid, semisolid, or liquid material acting as a vehicle, excipient, or medium for the active ingredient. Pharmaceutical unit dosage forms may be prepared for administration by any of several routes, including, but not limited to, oral and parenteral (especially by intramuscular and intravenous injection (in a vehicle other than oil), or by subcutaneous implant or transdermal administration.). Representative of such forms are tablets, soft and hard gelatin capsules, powders, lozenges, chewing gums, emulsions, suspensions, syrups, solutions, sterile injectable solutions, and sterile packaged powders. Composition containing a sulfonyl fluoride may be formulated by procedures known in the art so as to provide rapid, sustained, or delayed release of any or all of the compounds after administration.

As the sulfonyl fluoride formulation of the present invention is well suited to oral administration, preferred carriers will facilitate formulation in tablet or capsule form. Solid pharmaceutical excipients such as magnesium stearate, calcium carbonate, silica, starch, sucrose, dextrose, polyethylene glycol (PEG), talc, and the like may be used with other conventional pharmaceutical adjuvants including fillers, lubricants, wetting agents, preserving agents, disintegrating agents, flavoring agents, and binders such as gelatin, gum arabic, cellulose, methycellulose, and the like to form admixtures which may be used as such or may be tabulated, encapsulated, or prepared in other suitable forms as noted above. A general description of formulation is given in Remington's Pharmaceutical Sciences.

Administration is preferably by oral dosage but may be by transdermal application, intranasal spray, bronchial inhalation, suppository, parenteral injection (e.g., intramuscular or intravenous injection), and the like. Carriers for parenteral administration include, without limitation, aqueous solutions of dextrose, mannitol, mannose, sorbitol, saline, pure water, ethanol, glycerol, propylene glycol, peanut oil, sesame oil, polyoxyethylene-polyoxypropylene block polymers, and the like. One may additionally include suitable preservatives, stabilizers, antioxidants, antimicrobials and buffering agents, for example BHA, BHT, citric acid, ascorbic acid, tetracycline, and the like. Alternatively, one may incorporate or encapsulate a sulfonyl fluoride formulation in a suitable polymer matrix or membrane, thus providing a sustained-release delivery device suitable for implantation near the site to be treated locally. Other devices include indwelling catheters and devices such as the Alzet® minipump.

D. Combination Therapies

In order to increase the effectiveness of the sulfonyl fluoride therapy of the present invention, it may be desirable to combine these compositions with other agents effective in the treatment of cognitive disorders. Such agents include a wide variety of drugs including centrally active nicotinic agonists (to enhance acetylcholine release), muscarinic agonists (to enhance cholinergic function), drugs to protect against stroke-induced cell death, and drugs that rescue cells at risk of stroke-induced cell death or damage. The former agents have an additive effect to the known mechanism of cholinesterase inhibition induced by the sulfonyl fluoride. Insofar as the sulfonyl fluorides do not appear to protect against stroke-induced cell damage or death, the effect of the latter agents would be to preserve additional cells to enhance the overall effect of the sulfonyl fluoride through its action on larger populations of cells. These cells may be in the ischemic penumbra (immediately adjacent to the ischemic core) or regions distant to the stroke area (e.g., septum, hippocampus, or other areas important to cognitive functions).

It should be noted that most existing stroke pharmacologic treatments (thrombolytic agents such as the anticoagulant heparin, aspirin, and platelet inhibitors, as well as anti-excitotoxic N-methyl-D-aspartate antagonists like MK-801, and additional secondary drugs including calcium channel blockers, caspase inhibitors, free radical scavengers, and protein kinase inhibitors) target ischemic cells and cells in the ischemic penumbra. The sulfonyl fluorides appear to stimulate cells affected by the ischemic event as well as cells in brain regions distant from the stroke area. Thus, combining these two particular classes of drugs provide a particularly useful strategy for treating stroke.

Compositions are provided in a combined amount effective to confer a therapeutic benefit to a person suffering cognitive impairment resulting from an oxygen deficit. This process may involve administering the sulfonyl fluoride and the second agent(s) to the subject at the same time, for example, using a single composition or pharmacological formulation that includes both agents, or using two distinct compositions or formulations given at the same time, wherein one composition includes the sulfonyl fluoride and the other includes the second agent(s). Alternatively, the second agent therapy may precede or follow the sulfonyl fluoride treatment by intervals ranging from minutes to weeks.

The exact schedule of treatment with sulfonyl fluorides and second agent therapy is determined in large part by the pharmacokinetic or pharmacodynamic properties of the sulfonyl fluoride and the second agents. The sulfonyl fluorides typically have long pharmacodynamic effects with half-life times in hours or days, wherease the second agents have much shorter pharmacokinetic and pharmacodynamic effects, in the range of minutes to hours. These differences would dictate the most efficacious administration schedules and routes of administration.

In embodiments where the other agent and sulfonyl fluoride are administered separately to the subject, one may wish that a significant period of time did not expire between the time of each delivery, such that the second agent and sulfronyl fluoride would be able to exert an advantageously combined effect on the subject. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, sulfonyl therapy is "A" and the second agent is "B":

A/B/A B/A/B B/B/A A/A/B A/B/B B/A/A A/B/B/B B/A/B/B
B/B/B/A  B/B/A/B   A/A/B/B   A/B/A/B   A/B/B/A   B/B/A/A
B/A/B/A  B/A/A/B   A/A/A/B   B/A/A/A   A/B/A/A   A/A/B/A

Administration of the second agent will follow general protocols for the administration of sulfonyl fluoride, taking into account the toxicity, if any, of the agent. It is expected that the treatment cycles would be repeated as necessary.

As discussed above, most existing stroke pharmacologic treatments (thrombolytic agents such as the anticoagulant heparin, aspirin, and platelet inhibitors, as well as anti-excitotoxic N-methyl-D-aspartate antagonists like MK-801, and additional secondary drugs including calcium channel blockers, caspase inhibitors, free radical scavengers, and protein kinase inhibitors) target ischemic cells and cells in the ischemic penumbra. In contrast, the sulfonyl fluorides appear to stimulate cells affected by the ischemic event as well as cells in brain regions distant from the stroke area. However, the treatment of stroke by targeting brain areas distant from the ischemic area, using sulfonyl fluoride therapy against specific cholinergic systems (i.e., septal cholinergic areas, hippocampus, and/or cortical areas) is a novel approach to this type of therapy.

E. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Experimental Protocol. A total of 48 eight-week-old, male, Sprague-Dawley rats weighing about 250 g served as subjects in the present study. All animals were free of virus antibody. A 3-day acclimation period was allowed prior to using the animals. Animals were kept under a 12-12 hr light/dark cycle and allowed free access to food and water before and after surgical procedures. All experimental procedures followed UTEP IACUC guidelines for use of animals in research to minimize discomfort in the animals during surgery and in the recovery period. All tests were run blind, and the animal codes were revealed only at the end of the behavioral and histological analysis. In study one (n=24), the 0.3 mg/kg dose of MSF, which was previously reported as efficacious in ameliorating cognitive deficits in animals, was used to initially provide the putative drug's effects on ischemic animals. Studies two (dose response effects of MSF; n=16) and three (withdrawal of MSF; n=8) were conducted to further characterize the direct neurobehavioral effects of MSF. For study one, 16 animals underwent MCAo surgery, while eight animals underwent sham surgery. All animals in studies two and three received the ischemia surgery (see Table 1).

Ischemia/Reperfusion Surgery. Rats underwent the MCAo surgery as described elsewhere (Nishino et al., 1993; Borlongan et al., 1998a; 1998b). The MCAo embolic technique involved insertion of an embolic filament through the carotid artery to reach the junction of the MCA, thus blocking the blood flow from the common carotid artery, as well as from the Circle of Willis. Under deep anesthesia using chloral hydrate (400 mg/kg, i.p.), the right common carotid artery was identified and isolated through a ventral midline cervical incision. The embolus size was 4-0, made of sterile, non-absorbable suture (Ethicon, Inc.). The embolic tip was tapered to 24- to 26-gauge size using a rubber cement. About 15 to 17 mm of the embolic filament were inserted from the junction of the external and internal carotid arteries to block the MCA. The right MCA was occluded for one hour. Based on the studies and several others (Borlongan et al., 1998a; Borlongan et al., 1995a; 1995b), a one-hour occlusion of the MCA results in maximal infarction. In addition, the length and size of the tip of the embolus have been found to produce complete MCA occlusion in animals weighing 250 to 350 g (Borlongan et al., 1998a).

Behavioral Testing. At 4 wks after ischemia surgery, the elevated body swing test (EBST) and the passive avoidance test were performed to measure motor asymmetry and cognitive performance, respectively (Borlongan and Sanberg, 1995). Briefly, the EBST involves handling the animal by its tail and recording the direction of the swings made by the animal. The test apparatus consisted of a clear Plexiglas box (40×40×35.5 cm). The animal was gently picked up at the base of the tail, and elevated by the tail until the animal's nose was at a height of 2 inches (5 cm) above the surface. The direction of the swing, either left or right, was counted once the animal's head moved sideways approximately 10 degrees from the midline position of the body. After a single swing, the animal was placed back in the Plexiglas box and allowed to move freely for 30 seconds prior to retesting. These steps were repeated 20 times for each animal. The inventors have previously utilized the EBST, and noted that ischemic animals displayed>75% biased swing activity as early as 24 hrs post-ischemia surgery (Borlongan et al., 1998a; 1998b; 1998c).

The passive avoidance test followed the procedures described in detail elsewhere (Borlongan et al., 1998a; 1998b). Briefly, training and testing were carried out using a step-down passive avoidance box (27×27×30 cm; Lafayette Inst. Co.) made of Plexiglas. A Plexiglas platform shelf (7.5× 26.7×9.4 cm) was located in one corner of the box. Upon stepping off the platform, the rat received scrambled foot shock (approximately 2 mA; generated by a DC shock scrambler BRS Foringer No. SCS-003). Acquisition of the task was measured in terms of the amount of time it took the rat to remain on the platform continuously for 3 min. Twenty four hrs later, a retention test was conducted by placing the rat on the platform exactly as before and recording the latency to step-down measured to a maximum of 3 min. Ischemic animals display significant impairments in acquisition and retention of the task as early as 24 hrs post-ischemia that persist at least up to 6 months post-ischemia (Borlongan et al., 1998a; 1998b; 1998c).

Cerebral Infarction Assay. The triphenyltetrazolium chloride (TTC) staining procedures followed those described elsewhere (Wang et al., 1997). Randomly selected animals (n=4 per group) were sacrificed at 4 wks after MCAo surgery. Under deep anesthesia (chloral hydrate, 70 mg/kg, i.p.) animals were perfused intracardially with saline. The brain tissue was then removed, immersed in cold saline for 5 min, and sliced into 2.0 mm sections. The brain slices were incubated in 2% TTC dissolved in PBS for 30 min at 37° C. and then transferred to 5% formaldehyde solution for fixation. The volume of infarction, as revealed by negative TTC stains indicating dehydrogenase-deficient tissue, was measured in each slice and summed using computerized planimetry (PC-based Image Tools software). The volume of infarction=2 mm (thickness of the slice)×[sum of the infarction area in all brain slices (mm$^2$)] (Wang et al., 1997).

Choline Acetyltransferase (ChAT) Immunohistochemistry. Following the behavioral test at 4 wks post-ischemia, randomly selected animals (n=4 per group) were deeply anesthetized and perfused intracardially with 150 ml saline followed by 150 ml of 4% paraformaldehyde. The brains were post-fixed overnight in 4% paraformaldehyde and subsequently immersed in 20% sucrose in 4% paraformaldehyde and stored at 8° C. until sectioning. A vibratome (Vibroslice, Fla.) was used to cut the brain (40 µm sections). Ten serial brain sections that included the septal region (+1.4 to +0.2 mm from the bregma) were processed for ChAT immunohistochemistry. Sections were pre-incubated in 5% blocking serum (normal goat, Jackson ImmunoResearch Laboratories, PA) in 0.1% Triton-X in 0.1 M NaPBS for 60 min, followed by incubation in the primary ChAT antibody (Boehringer Mannheim Biochemical, IN; 1:10 dilution in 0.1 M phosphate-buffered saline, NaPBS) at room temperature overnight. The sections were reacted with the appropriate biotinylated secondary antibody (1:2000) for 45 min, followed by an avidin-biotin-peroxidase complex system (ABC Elite Vectastain Kit, Vector, Burlingame, Calif.) for 45 min. Finally, the Vector VIP Kit (Vector, Burlingame, Calif.) was used to visualize the reaction product. The sections were mounted on gelatin-coated glass slides, dried overnight, dehydrated in increasing alcohol concentrations, and coverslipped using Permount (Fisher Scientific, Pittsburgh, Pa.) mounting solution. Serial sections were digitized using a PC-based Image Tools computer program. To determine the ChAT alterations in the septum, comparisons of mean total number (average counts from ten brain sections per animal) of septal ChAT-immunoreactive (ir) neurons from MSF- and vehicle-treated ischemic animals were conducted. Individual counts of ChAT-ir neurons were made using the following criteria: heavily stained nuclei (HN), pale stained nuclei (PN) and presence of elaborate processes (P). Each criterion or combined counts of nuclei and processes were used as raw data for statistical analyses. In addition, a 5-point semi-quantitative scale was used to assess the intensity of ChAT immunoreactivity. These evaluations helped to characterize the morphology of ChAT-ir neurons. Two observers blind to treatment conditions carried out the examination of CHAT immunoreactivity.

Control Acetylcholinesterase Assays. Two additional groups of normal control (non-ischemic) rats were treated with MSF (N=4) or peanut oil vehicle (N=4) in accordance with the exact procedures used with the other groups in order to estimate the level of acetylcholinesterase inhibition produced. At the end of the study, the rats were sacrificed and acetylcholinesterase assays were conducted at 25° C. according to the spectrophotometric method (Ellman et al., 1961) with minor modifications (pH set at 7.4 and using 1 mM acetyl-β-methyl-thiocholine iodide as substrate).

Drugs. For study 1, animals received ip injections of either MSF (1 mg/kg at 24 and 48 hrs post-MCAo and 0.3 mg/kg thereafter every other day) or the vehicle, peanut oil, for four weeks. Each animal received 0.5 ml of the solution. For study 2, animals received 1 mg/kg at 24 and 48 hrs post-MCAo and 0, 0.15, 0.30 or 0.6 mg/kg of MSF in peanut oil using the same regimen mentioned above. For study 3, animals were introduced to the same regimen as in study 1, but thereafter received peanut oil every other day from four weeks up to eight weeks post-MCAo.

Statistical Analyses. Animals were tested twice (24-hr interval between test sessions) in each behavioral test and the individual averages were used as raw data. Student t-test was used to evaluate statistical differences between MSF- and vehicle-treated groups. Differences were considered significant at p<0.05. Values are expressed as means±S.E.M.

Example 2

Results

Acetylcholinesterase Inhibition. As expected from earlier reports, MSF treatment produced profound inhibition of acetylcholinesterase. Whole brain acetylcholinesterase activity, estimated from assays of half of whole brain, was 90.2% inhibited compared to the peanut oil controls. Specific brain parts, dissected from the other half of the brains showed similar inhibition: 88.5% in hippocampus, 85.9% in cortex and 95.0% in striatum/nucleus accumbens.

MSF Does Not Protect Against Ischemia-Induced Motor Asymmetry. Ischemic animals that received MSF exhibited 87.7±8% biased swing activity, while those that were treated with vehicle displayed 84.8±10% biased swing activity (FIG. IA). There were no significant differences in the motor asymmetries between the two groups (p>0.05), indicating that MSF did not correct the biased motor behaviors induced by unilateral ischemia.

Figure 1B:
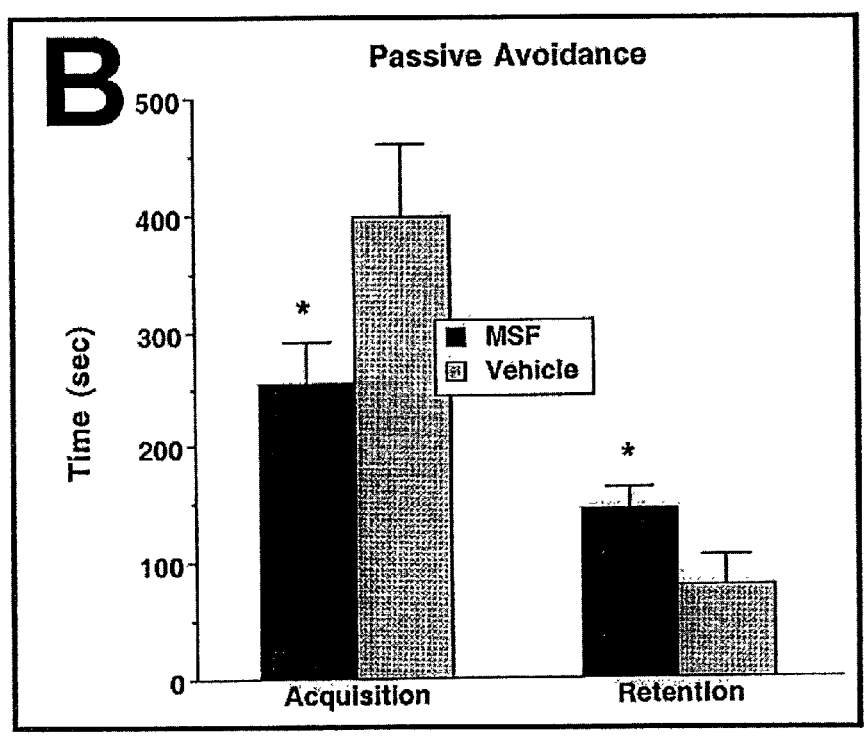

MSF Ameliorates Ischemia-Induced Passive Avoidance Deficits. Ischemic animals that received MSF acquired the task (255±36 sec) in a significantly shorter time than ischemic animals that received the vehicle (398±62 sec) (p<0.05) (FIG. 1B). In addition, MSF-treated ischemic animals retained the task in a significantly longer time (145±18 sec) than vehicle-treated ischemic animals (79±26 sec) (p<0.05). Thus, MSF preserved near normal acquisition and retention of the passive avoidance task in ischemic animals.

MSF Does Not Protect Against Cerebral Infarction. Ischemic animals treated with vehicle had a mean volume of 87.4±9.4 mm$^3$ of infarcted tissue, while ischemic animals treated with MSF had 78.1±14.2 mm$^3$ infarction (FIG. 2). These volumes of infarction between the two groups were not significantly different (p>0.05). The core of infarction was located around the lateral aspect of the striatum, with portions of the medial striatum and the lateral frontal cortex immediately adjacent to the ischemic core identified as the ischemic penumbra. The core of infarction displayed a small area of tissue loss surrounded by some necrosis. The rest of the TTC-deficient brain sections, mainly consisted of the lateral striatum, revealed widespread cell loss but the tissues remained intact. The TTC data showed that MSF was not effective against necrotic cell death associated with ischemia. Preliminary results also noted that MSF did not block ischemia-induced apoptotic cell death.

Figure 3A:
FIGS. 3A-3C: The effect of MSF on septal ChAT immunoreactivity. Compared to vehicle-treated ischemic animals (FIG. 3A), MSF-treated ischemic animals (FIG. 3B) displayed enhanced septal ChAT immunoreactivity characterized by heavily stained nuclei (HN) and elaborate processes (P) forming clusters of dense networks of fibers, which can be found along the medical septum and the lateral septum. Further examination of the morphology of the ChAT-ir cells revealed significant increments (10%-15%) in mean total number of HN+P and HN in MSF-treated ischemic animals compared to vehicle-treated ischemic animals (FIG. 3C). Asterisk (*) indicates significance at p<0.05. PN means pale nuclei. The scale bar is 250 μm.
Figure 3B:
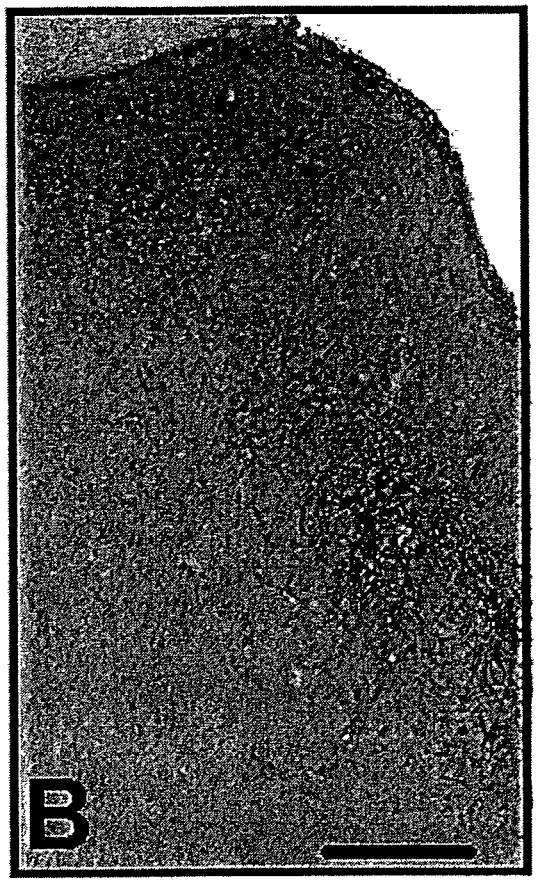
Figure 3C:
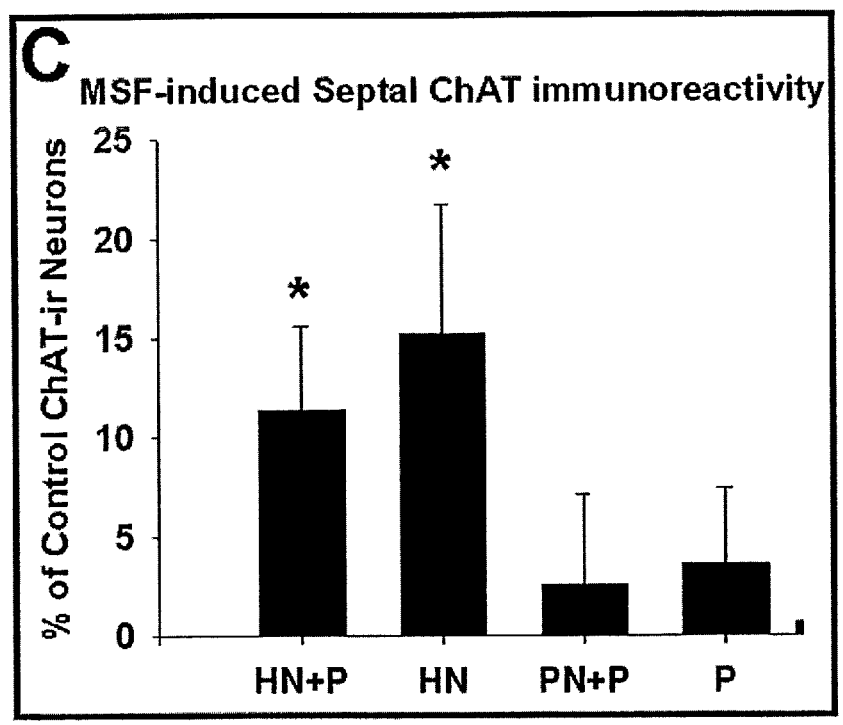

MSF Enhances Septal ChAT Immunoreactivity. Ischemic animals that were treated with MSF showed more intense staining of ChAT-ir neurons in the lateral and medial septum compared to vehicle-treated ischemic animals. The septal CHAT immunoreactivity of MSF-treated ischemic animals was characterized by heavily stained nuclei that were noted in clusters along the intermedialis area of the lateral septum and the medial septum (FIG. 3). From the heavily stained nuclei, elaborate ChAT-ir fibers of MSF-treated ischemic animals formed denser networks than those seen in vehicle-treated ischemic animals. Furthermore, MSF-treated ischemic animals demonstrated larger somas of ChAT-ir neurons with long processes and extensive dendritic arborizations compared to those of vehicle-treated ischemic animals (Table 2). There were no obvious differences in the ChAT immunoreactivity between the ipsilateral (to the ischemic side) and the contra-lateral septum when comparing within treatment groups. However, the general septal ChAT immunoreactivity appears to be increased in the MSF-treated animals than the vehicle-treated ischemic animals.

Example 3

Discussion

The present inventors have demonstrated the efficacy of MSF in ameliorating the cognitive deficits in ischemic adult rats. This positive effect was noted despite the lack of protective effects of MSF on the ischemia-induced cerebral infarction. The observed increase in septal ChAT immunoreactivity in MSF-treated animals suggests that normal cognitive tasks can be preserved by specifically enhancing the activity of this group of cholinergic neurons outside the infarcted brain area.

Previously, chronic MSF treatment has been demonstrated to enhance the acquisition of a one-trial per day discriminative reward learning task in middle-aged and older rats (Malin et al., 1991; 1993). Because MSF is a selective inhibitor of AChE (Pacheco et al., 1995), this minimizes toxic side effects seen with non-selective AChE inhibitors. Indeed, chronic MSF treatment even at the low dose of 0.22 mg/kg given three times per week produces a significant decrement (about 50%) in brain AChE activity, but without discernable locomotor side effects and no liver damage (Malin et al., 1993). Similarly, brain AChE activity is reduced by 70% after a single systemic injection of 1.5 mg/kg MSF with no observable behavioral alterations (Moss et al., 1985).

Memory dysfunctions have been consistently correlated with abnormal synthesis of acetylcholine in the brains of Alzheimer's disease (AD) patients. Indeed, the cholinergic hypothesis, which states that a serious loss of cholinergic function in the CNS contributes significantly to the cognitive symptoms of AD, has been advanced over the last 20 years (Bartus, 2000). Recently, a double-blind, placebo-controlled study concluded that MSF produces significant clinical improvements in the cognitive performance of SDAT patients (Moss et al., 1999). Such cognition-enhancing effects of MSF persisted up to eight weeks after withdrawal of the drug.

Here the inventors presented surprising data supporting the utility of MSF for treatment of cognitive dysfunctions associated with cerebral ischemia. The dichotomy of CNS control over motor behavior and cognitive function is exemplified in the present results. Since administration of MSF 24 hrs post-stroke did not protect against striatal and cortical infarction, both MSF- and vehicle-treated ischemic animals displayed similar asymmetrical behaviors. Surprisingly, MSF enhanced septal ChAT immunoreactivity, and MSF-treated ischemic animals exhibited better cognitive performance in the passive avoidance task than vehicle-treated ischemic animals. A 27% reduction in ChAT-ir neurons has been shown to coincide with significant performance deficits on water maze and other motor tasks in mice with null mutations in the neurotrophin receptor p75 (Peterson et al., 1999), while treatment with nerve growth factor can protect against decrements in ChAT-ir neurons, as well as memory impairments induced by brain insults (Dixon et al., 1997; Wortwein et al., 1998). The differential effects of MSF on motor and cognitive performance imply that near normal cognitive functions can be preserved even with concomitant cerebral infarction. These observations have direct clinical applications because MSF treatment may offer stroke patients with existing cerebral infarction a method to recover their cognitive skills.

The absence of observable protective effects of MSF on cerebral infarction may be due to the limited window of treating stroke with pharmacologic agents. Because CNS neurons begin to degenerate rapidly after the onset of ischemia, the brain tissue (the necrotic ischemic core) deprived of oxygen and glucose cannot be rescued from neuronal degeneration by current methods. On the other hand, the ischemic penumbra (the periphery of the injured vascular territory) can be normalized with timely restoration of the blood flow (Pulsinelli et al., 1997). Accordingly, the ischemic penumbra is a target area for prevention of neuronal degeneration, as well as restoration of function following a stroke episode (Iadecola and Ross, 1997). Commencing MSF treatment 24-hr post-stroke may be too late to rescue the ischemic neurons. Indeed, pretreatment with another AChE inhibitor, ENA-173, has been shown to preserve the levels of hippocampal acetylcholine and to protect against ischemia-induced loss of pyramidal cells in the hippocampas (Sadoshima et al., 1995; Tanaka et al., 1994). Alternatively, MSF may act solely on cholinergic neurons, which represent only a subset of many neuronal populations altered following ischemia. The inventors believe that MSF, in combination with other drugs, may protect additional neuronal populations besides cholinergic neurons to enhance post-ischemic rehabilitation and to achieve protection against isehemic cell death.

In summary, the inventors described for the first time that the AChE inhibitor MSF maintained nearly normal cognitive performance in adult rats subjected to experimental stroke. While it did not exert protective effects against cerebral infarction, MSF increased septal ChAT immunoreactivity, which along with cholinesterase inhibition, contributed to the preservation of memory functions in MSF-treated ischemic animals.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 5,798,392

Ashford, Soldinger, Schaeffer, Cochran, Jarcvik, "Physostigmine and its effect on six patients with dementia," *Am. J. Psychiatry*, 138:829-830, 1981.

Bartus, "On neurodegenerative diseases, models, and treatment strategies: lessons learned and lessons forgotten a generation following the cholinergic hypothesis," *Exp. Neurol.*, 163:495-529, 2000.

Borlongan and Sanberg, "Elevated body swing test: a new behavioral parameter for rats with 6-hydroxydopamine-induced hemiparkinsonism," *J. Neurosci.*, 15:5372-5378, 1995.

Borlongan Cahill, Sanberg, "Locomotor and passive avoidance deficits following occlusion of the middle cerebral artery," *Physiol. Behav.*, 58:909-917, 1995a.

Borlongan, Martinez, Shytle, Freeman, Cahill, Sanberg, "Striatal dopamine-mediated motor behavior is altered following occlusion of the middle cerebral artery," *Pharmacol. Biochem. Behav.*, 52:225-229, 1995b.

Borlongan, Hida, Nishino, "Early assessment of motor dysfunctions aids in successful occlusion of the middle cerebral artery," *Neuroreport.*, 9:3615-3621, 1998a.

Borlongan, Tajima, Trojanowski, Lee, Sanberg, "Cerebral ischemia and CNS transplantation: differential effects of grafted fetal rat striatal cells and human neurons derived from a clonal cell line," *Neuroreport.*, 9:3703-3709, 1998b.

Borlongan, Tajima, Trojanowski, Lee, Sanberg, "Transplantation of cryopreserved human embryonal carcinoma-derived neurons (NT2N cells) promotes functional recovery in ischemic rats," *Exp. Neurol.*, 149:310-321, 1998c.

Deutsch, "The cholinergic synapse and the site of memory," *Science*, 174:788-794, 1971.

Dixon, Flinn, Bao, Venya, Hayes, "Nerve growth factor attenuates cholinergic deficits following traumatic brain injury in rats," *Exp. Neurol.*, 146:479-490, 1997.

Dobkin, "Activity-dependent learning contributes to motor recovery," *Ann. Neuro.*, 144:158-160, 1998.

Drachman and Glosser, "Pharmacological strategies in aging and dementia: the cholinergic hypothesis," *In: Strategies for the Development of an Effective Treatment of Senile Dementia*, Crook and Gershon (Eds.), Mark Powley Associates, New Canaan, Conn., 35-54, 1981.

Ellman, Courtney, Andres Jr., Featherstone, "A new and rapid colorimetric determination of acetylcholinesterase activity," *Biochemical Pharmacology*, 7: 88-95, 1961.

Endres, Namura, Shimizu-Sasamata, Waeber, Zhang, Gomez-Isla, Hyman, Moskowitz, "Attenuation of delayed neuronal death after mild focal ischemia in mice by inhibition of the caspase family," *J. Cereb. Blood Flow Metab.*, 18:238-247, 1998.

Iadecola and Ross, "Molecular pathology of cerebral ischemia: delayed gene expression and strategies for neuroprotection," *Ann. NY Acad. Sci.*, 835:203-217, 1997.

Lee, Zipfel, Choi, "The changing landscape of ischaemic brain injury mechanisms," *Nature*, 399:A7-A14, 1999.

Macko, DeSouza, Tretter, Silver, Smith, Anderson, Tomoyasu, Gorman, Dengel, "Treadmill aerobic exercise training reduces the energy expenditure and cardiovascular demands of hemiparetic gait in chronic stroke patients," *Stroke*, 28:326-330, 1997.

Malin, Plotner, Radulescu, Ferebee, Lake, Negrete, Schaefer, Crothers, Moss, "Chronic methanesulfonyl fluoride enhances one-trial per day reward learning in aged rats," *Neurobiol. Aging*, 14:393-395, 1993.

Malin, Toups, Osgood, Fowler, Hunter, Arcangeli, Moss, "Chronic methanesulfonyl fluoride enhances one-trial reward learning in mid-aged rats," *Neurobiol. Aging*, 12:181-183, 1991.

Moss, Berlanga, Hagan, Sandoval, Ishida, "Methanesulfonyl fluoride (MSF): a double-blind, placebo-controlled study of safety, and efficacy in the treatment of senile dementia of the Alzheimer type," *Alzheimer Dis. Assoc. Disord.*, 13:20-25, 1999.

Moss, Kobayashi, Pacheco, Palacios, Perez, "Methanesulfonyl fluoride: A CNS selective Cholinesterase inhibitor," *In: Current Research in Alzheimer Therapy*, Giacbini and Becker (Eds.), Taylor and Francis, New York City, 305-314, 1988.

Moss, Rodriguez, McMaster, "Comparative behavioral effects of CNS cholinesterase inhibitors," *Pharmacol. Biochem. Behav.*, 22:479-482, 1985.

Nishino, Koide, Aihara, Kumazaki, Sakurai, Nagai, "Striatal grafts in the ischemic striatum improve pallidal GABA release and passive avoidance," *Brain Res. Bull.*, 32:517-520, 1993.

Nishino, Kumazaki, Sakurai, Sanberg, Borlongan, "Melatonin protects against deficits associated with occlusion of the middle cerebral artery in adult rats," *Soc Neurosci. Abstr.*, 24:213, 1998.

Pacheco, Palacios-Esquivel, Moss, "Chholinesterase inhibitors proposed for treating dementia in Alzheimer's disease: selectivity toward human brain cetylcholinesterase compared with butyrylcholinesterase," *J. Pharmacol. Exp. Ther.*, 274:767-770, 1995.

Peterson, Dickinson-Anson, Leppert, Lee, Gage, "Central neuronal loss and behavioral impairment in mice lacking neurotrophin receptor p75," *J. Comp. Neurol.*, 404:1-20, 1999.

Pulsinelli, Jacewicz, Levy, Petito, Plum, "Ischemic brain injury and the therapeutic window," *Ann. NY Acad. Sci.*, 835:187-192, 1997.

Reutter, Filbert, Moore, Adler, "A role for butyrylcholinesterase in respiratory pathophysiology following nerve agent intoxication," *In: Proceedings of the Sixth Medical Chemical Defense Biosciences Review*, U.S. Army Medical Research and Development Command, U.S. Army Medical Institute of Chemical Defense, Aberdeen Proving Ground, MD, 393-396, 1987.

Sadoshima, Ibayashi, Fujii, Nagao, Sugimori, Fujishima, "Inhibition of acetylcholinesterase modulates the autoregulation of cerebral blood flow and attenuates ischemic brain metabolism in hypertensive rats," *J. Cereb. Blood Flow Metab.*, 15:845-851, 1995.

Schellinger, Orberk, Hacke, "Antithrombotic therapy after cerebral ischemia," *Fortschr Neurol. Psychiatr.*, 65:425-434, 1997.

Siesjo, Carlsson, Hagerdal, Nordstrom, "Brain metabolism in the critically ill," *Crit. Care Med.*, 4:283-294, 1976.

Tanaka, Ogawa, Mizukawa, Asanuma, Kondo, Nishibayashi, Mori, "Acetylcholinesterase inhibitor ENA-713 protects against ischemiainduced decrease in pre- and postsynaptic cholinergic indices in the gerbil brain following transient ischemia," *Neurochem. Res.*, 19:117-122, 1994.

Wang, Lin, Chiou, Williams, Hoffer, "Glial cell line-derived neurotrophic factor protects against ischemia-induced injury in the cerebral cortex," *J. Neurosci.*, 17:4341-4348, 1997.

Wettstein, "No effect from double blind trial of physostigmine and lecithin in Alzheimer disease," *Ann. Neurol.*, 13:210-212, 1982.

Wortwein, Yu, Toliver-Kinsky, Perez-Polo, "Responses of young and aged rat CNS to partial cholinergic immunolesions and NGF treatment," *J. Neurosci. Res.*, 52:322-333, 1998.

What is claimed:

1. A method of treating a mammal for cognitive deficits resulting after an oxygen deficit in the brain comprising the step of administering to said mammal, within 24 hours of said deficit, a dose of a sulfonyl fluoride effective to treat said oxygen deficit in the brain, wherein said sulfonyl fluoride is selected from the group consisting of methanesulfonyl fluoride and ethanesulfonyl fluoride.

2. The method of claim 1, wherein said oxygen deficit is caused by stroke, trauma, carbon monoxide poisoning, and other poisonings.

3. The method of claim 1, wherein said dose of sulfonyl fluoride is about 0.01 mg/kg to about 20 mg/kg.

4. The method of claim 1, wherein said dose of sulfonyl fluoride is about 0.05 mg/kg to about 5 mg/kg.

5. The method of claim 1, wherein said dose of sulfonyl fluoride is about 0.15 mg/kg to about 0.5 mg/kg.

6. The method of claim 1, wherein said sulfonyl fluoride is administered in a pharmaceutically acceptable excipient.

7. The method of claim 1, further comprising co-administering with said sulfonyl fluoride a second therapeutic agent that also treats said oxygen deficit in the brain.

8. The method of claim 7, wherein said second therapeutic agent comprises a therapeutically effective dose of an agent selected from the group consisting of glutamate release modulators, acetylcholine synthesis enhancers, nicotinic agonists, muscarinic agonists, thrombolytic agents, a cholesterol reducing agent, an anti-excitotoxic N-methyl-D-aspartate antagonist, a calcium channel blocker, a cholinergic agonist, a caspase inhibitor, a free radical scavengers, or a protein kinase inhibitor.

9. The method of claim 8, wherein the thrombolytic agent is heparin, aspirin, or a platelet inhibitor.

10. The method of claim 8, wherein the anti-excitotoxic N-methyl-D-aspartate antagonist is dizocilipine maleate.

11. The method of claim 8, wherein the cholinergic agonist is 2-ethyl-8-methyl-2,8 diazospiro [4.5]-decane-1,3-dione hydrobromide.

12. The method of claim 8, wherein the acetylcholine synthesis enhancer is lecithin.

13. The method of claim 8, wherein the glutamate release modulator is 4-aminopyridine.

14. A method of reducing one or more stroke-induced cognitive deficits in a mammal comprising the step of administering to said mammal, within 24 hours of said stroke, a dose of a sulfonyl fluoride selected from the group consisting of methanesulfonyl fluoride and ethanesulfonyl fluoride, said dose effective to reduce one or more stroke-induced cognitive deficits.

15. A method of reducing stroke-induced loss of function in a tissue distal to the stroke site in a mammal comprising the step of administering to said mammal, within 24 hours of said stroke, a dose of a sulfonyl fluoride selected from the group consisting of methanesulfonyl fluoride and ethanesulfonyl fluoride, said dose effective to protect from stroke-induced loss of function at said distal tissue.

* * * * *